United States Patent [19]

Feibush et al.

[11] Patent Number: 5,277,813
[45] Date of Patent: Jan. 11, 1994

[54] SHIELDED STATIONARY PHASES

[75] Inventors: Binyamin Feibush, State College, Pa.; Daryl J. Gisch, Midland, Mich.

[73] Assignee: S.A.C. Corporation, St. Louis, Mo.

[21] Appl. No.: 988,610

[22] Filed: Dec. 10, 1992

Related U.S. Application Data

[63] Continuation of Ser. No. 557,333, Jul. 23, 1990, abandoned, which is a continuation-in-part of Ser. No. 208,200, Jun. 17, 1988, abandoned.

[51] Int. Cl.⁵ ............................................. B01D 15/08
[52] U.S. Cl. ............................... 210/502.1; 210/635; 210/656; 210/198.2; 502/401
[58] Field of Search ............... 210/635, 656, 198.2, 210/502.1; 502/401, 402, 407; 530/413

[56] References Cited

U.S. PATENT DOCUMENTS

| | | | |
|---|---|---|---|
| 3,960,720 | 6/1976 | Porath et al. | 210/198.2 |
| 4,118,316 | 10/1978 | Talley et al. | 210/198.2 |
| 4,177,038 | 12/1979 | Biebricher et al. | 210/656 |
| 4,411,795 | 10/1983 | Olson | 210/679 |
| 4,450,486 | 9/1985 | Ramsden | 210/198.2 |
| 4,544,485 | 10/1985 | Pinkerton et al. | 210/502.1 |
| 4,705,725 | 11/1987 | Glajch et al. | 428/405 |
| 4,721,573 | 1/1988 | Ramsden et al. | 210/635 |
| 4,778,600 | 10/1988 | Williams | 210/198.2 |
| 4,782,040 | 11/1988 | Revis et al. | 502/401 |
| 4,927,879 | 5/1990 | Pidgeon | 210/656 |
| 4,931,498 | 6/1990 | Pidgeon | 210/656 |
| 4,996,343 | 1/1991 | Karger et al. | 210/656 |
| 5,045,190 | 9/1991 | Carbonell et al. | 210/198.2 |

OTHER PUBLICATIONS

D. J. Gisch et al., Journal of Chromatography, 433, (1988) 264-268.

G. Tamai et al., Chromatographia 21, No. 9, (1986) 519-522.

H. Yoshida et al., Chromatographia, vol. 19 (1985) 466-472.

R. A. Hux et al., Anal. Chem. 54, 1982, 113-117.

S. F. Chang et al., J. Pharm. Sci. 72, No. 3, 1983, 236-239.

W. Roth et al., J. of Chromatography, 222, 1981 13-22.

A. Helenius et al., Biochimica et al., Biphysica Acta 415, (1975) 29-79.

M. Freifelder, J. Amer. Chem. Soc., Col. 82, May 1960, 2386-2389.

J. G. Dorsey, Chromatography, vol. 2, No. 4, (1987) 13-20.

Snyder, Introduction to Modern Liquid Chromatography, 1979, 270-278.

*Primary Examiner*—Ernest G. Therkorn
*Attorney, Agent, or Firm*—Senniger, Powers, Leavitt & Roedel

[57] ABSTRACT

Novel packing materials are provided for liquid chromatography and/or solid phase extraction columns which will allow direct injection of biological fluids. These packing materials have a hydrophilic exterior layer and a hydrophobic, charged or otherwise selective portion that forms an underlayer or is embedded in the hydrophilic layer. During a chromatographic process large water soluble biopolymers will be in contact with the hydrophilic outer layer and be shielded from interacting with the underlayer or embedded portion and elute unretained. Small analytes, on the other hand, can be fully partitioned throughout the exterior and interior layers and are retained by hydrophobic or electrostatic interactions. Using such packings the direct analyses of plasma or serum for drug analysis is demonstrated.

6 Claims, 8 Drawing Sheets

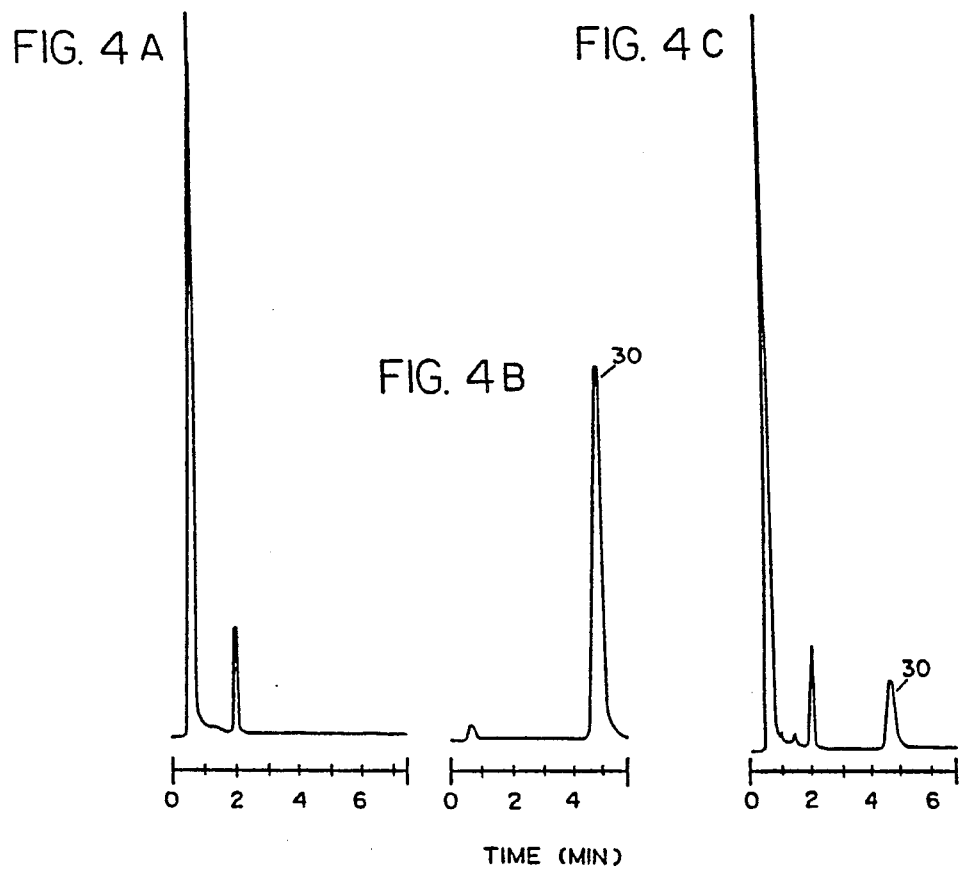
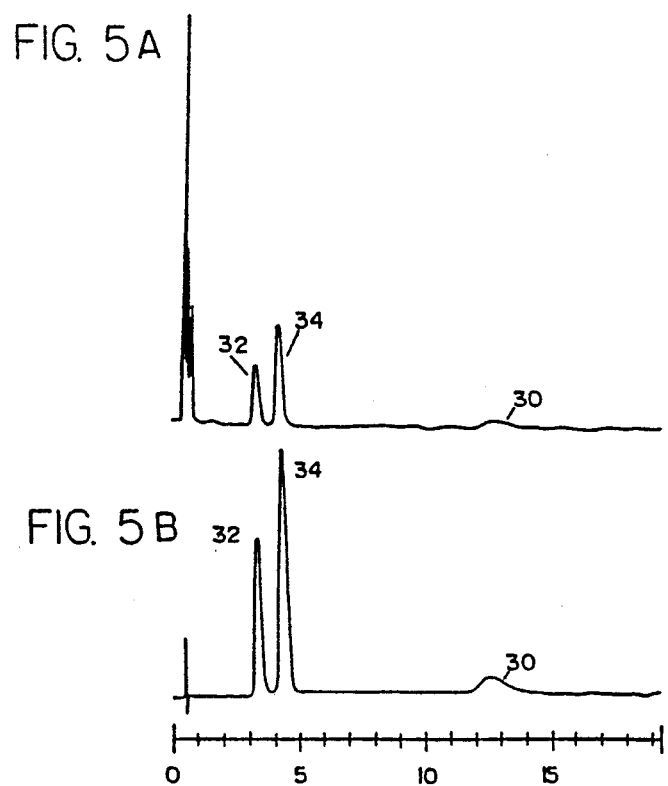

TIME (MIN)

TIME (MIN)

SHIELDED STATIONARY PHASES

This is a continuation of application Ser. No. 557,333, filed Jul. 23, 1990, now abandoned, which, in turn, is a continuation-in-part of application U.S. Ser. No. 208,200, filed Jun. 17, 1988, now abandoned.

This invention relates to the separation of compounds having a molecular weight of less than 1000 daltons from bio-polymers. In particular, it relates to novel packing supports useful in liquid chromatography (LC) and solid phase extraction (SPE) techniques for separating drugs, metabolites, etc. from mixtures containing water soluble proteins.

BACKGROUND OF THE INVENTION

It is frequently necessary to confirm the presence of drug substances, their metabolites, etc., in serum or plasma and/or to measure the concentrations of these compounds. In other cases, it is necessary to separate bio-polymers from smaller substances as a step in purifying substances from biological or from biomass mixtures. Such analyses are carried out using liquid chromatographic systems as illustrated in FIG. 1 of the drawings. The invention is compatible with high performance liquid chromatographic systems but is not limited to them.

Most of the published data and methods in this area of research relate to the LC analysis of drugs, metabolites, etc., in serum or plasma. The ways the mixtures are sampled can be classified as indirect and direct sampling. Indirect sampling involves treatment of the sample to remove the proteins, e.g. by precipitation, followed by extraction of the compound(s) of interest into a protein-free solvent system. Although this method involves multi-step preparation before the sample can be analyzed by a particular LC method, it still attracts much of the practical attention. Direct sampling, or direct injection of the untreated sample on an LC analytical column, causes clogging of the column, resulting in increasing pressure drop, peak broadening, variation of retention times, etc., unless special precautions are taken. After each sample injection, or after a few injections, the column must be thoroughly washed to remove precipitated proteins, particularly when larger serum samples ($\geq 10$ $\mu$l) are needed to detect the analytes of interest at their therapeutic or biological levels.

A partial solution to the above problems was found in a combination of an analytical column and a precolumn and two delivery pumps in a column switching system. Usually, the serum sample is loaded onto a short precolumn under mobile phase conditions in which only the drug(s) elute onto the analytical column. When all the components of interest elute from the precolumn to the analytical column, a valve is switched so that one pump continues to deliver mobile phase for elution of the compounds of interest from the analytical column for separation, while the second pump delivers a washing solution to the precolumn for removal of the proteins. To avoid clogging, the precolumn is filled with relatively large particles, usually 20-40 $\mu$m, and is replaced frequently to avoid deterioration of the analytical column (W. Rothe, et al., J. Chromatog. 222 (1981) 13). Usually, both columns are filled with reversed phase packing, e.g. $C_8$ or $C_{18}$ bonded to a silica support.

To avoid protein accumulation in the precolumn and to speed up the washing step, a less hydrophobic packing has been used, butyl modified methacrylate, as manufactured by TosoH, Japan, and sold under the tradename TOYOPEARL TM BT-650M. In the loading cycle, 10-50% saturated ammonium sulfate $(NH_4)_2SO_4$ aqueous mobile phase is used. Under such conditions, serum proteins are retained on the precolumn and the drugs elute to load the reversed phase analytical column. Then, by column switching, the analytical column is separately programmed, while the precolumn is cleaned of the retained proteins, using a buffer solution of lower ionic strength (G. Tamai, et al., Chromatographia 21 (1986) 519).

In another study, a polystyrene divinylbenzene resin, manufactured by Rohm and Haas, USA, and sold under the tradename Amberlite® XAD-2, was used as the packing in the precolumn to retain methaqualone (MTQ), while eluting the plasma proteins. After all the proteins were washed away (with a pH 9.3 buffer solution), the mobile phase is adjusted to elute MTQ (R. A. Hux, et al., Anal. Chem. 34 (1982) 113).

Another example of a two-modal HPLC system combines size exclusion chromatography (SEC) and reversed phase chromatography (RPLC) using two columns in a column switching system. Following exclusion of the biopolymers from the SEC column, the later eluting band of smaller molecular size compounds was backflushed to the RPLC analytical column (S. F. Chang, et al., J. Pharm. Sci. 72 (1983) 236).

All the above examples employ column switching which requires an elaborate chromatographic system, including a second solvent delivery system, a second column and a switching system. Moreover, the operation of the switching system itself requires labor or investment in additional control equipment.

A completely different approach was undertaken by Pinkerton, et al. (U.S. Pat. No. 4,544,485). They redesigned the packing of the analytical column in such a way that the proteins elute in the excluded volume (void volume) and the analytes are retained and separated on the same analytical column. This was accomplished by chemically modifying a hydrophilic diol phase with a hydrophobic oligopeptide, e.g. glycyl-(L-phenylalanine)n, where n=1,2, or 3. It is crucial to their invention that the diol phase is bonded to a porous silica gel having a pore diameter smaller than 80 angstroms. Following this modification, the phenylalanine moiety is enzymatically cleaved from the diol ligand with a protease. The cleavage is restricted to surface areas that are accessible to the protease, resulting in a support for which the diol ligands are only present on the external surface, while L-phenylalanine modified ligands are present in the internal surface, i.e., the pores of the packing material. The ligands that are not accessible to the enzyme are similarly not accessible to the serum proteins. Thus, these proteins are excluded from entering the pores and elute in the void volume, while the smaller molecules (e.g., drugs) can interact with the hydrophobic phenylalanine ligands (U.S. Pat. No. 4,544,485). This support, named internal surface reverse phase liquid chromatographic packing (IS-RP), can be used to analyze many serum sample without the damaging accumulation of proteinaceous precipitate seen on regular RPLC columns.

Conceptually, the study of Yoshida, et al., (Chromatographia 19 (1985) 466) is similar to that of Pinkerton. They adsorbed denatured plasma proteins on $C_{18}$ silica supports having small pore diameter. These supports no longer retained plasma proteins, but still showed reversed phase characteristics for smaller analytes. The phenomenon is depicted as similar to that of Pinkerton's model, or as having the proteinaceous precipitation limited to the externally exposed surface, thereby making the external surface hydrophilic, while keeping the non-exposed internal $C_{18}$ surface free of such precipitation and accessible for (hydrophobic) interaction with small compounds.

Thus an object of this invention is to provide a novel packing material for liquid chromatography which will allow the direct injection of biological fluids into the column.

Another object of this invention is to provide a packing material for chromatographic columns which has a hydrophilic exterior layer and a hydrophobic underlayer.

Still another object of this invention is to provide a chromatographic column which will shield and exclude large biopolymers but permit the partitioning of and hydrophobic interaction with small analytes.

Yet another object of this invention is to provide a novel shielded hydrophobic phase packing for chromatography adapted to bond to porous and non-porous silica supports.

Another object of this invention is to provide a chromatographic phase having a covalently bonded micellar surface.

Another object of this invention is to provide a packing material for chromatographic columns which has a hydrophilic exterior layer and an anionic underlayer.

Another object of this invention is to provide a packing material for chromatographic columns which has a hydrophilic exterior layer and a cationic underlayer.

Another object of this invention is to provide a packing material for chromatographic columns which has a hydrophilic exterior layer and a chelating underlayer.

These and other objects of this invention may be seen by reference to the present specifications, claims, and drawings.

THE INVENTION

We have discovered shielded stationary-phase packing materials useful for liquid chromatography analysis and/or solid-phase extraction of mixtures containing proteinaceous compounds and small analytes, comprising:
a support;
an internal leash bonded to the support and bearing functionality that interacts with the small analytes; and
an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds.

In an alternative embodiment, we have discovered a shielded stationary-phase packing material for liquid chromatography analysis and/or solid-phase extraction of mixtures containing proteinaceous compounds and small analytes, comprising:
a support;
a hydrophilic polymeric network covalently bonded to the support; and
regions embedded within the network which contain functionality which interacts with the small analytes;
whereby small analytes will diffuse through the network and interact with the embedded regions and proteinaceous compounds will be excluded from such interaction.

We have further discovered a method of making these shielded stationary-phase packing materials, chromatography columns packed with these shielded stationary-phase packing materials, a method of liquid chromatographic separation which uses these chromatography columns, and a method of solid-phase extraction which uses these shielded stationary-phase packing materials.

DETAILED DESCRIPTION OF THE INVENTION

The present invention is a new concept providing novel LC or SPE packing materials which discriminate between water soluble proteins and smaller analytes on the bases of hydrophobic, ionic or other interactions. The novel LC or SPE packings of the present invention are (bonded) porous or non-porous supports in which an external, polar hydrophilic layer shields an underlayer which interacts with the small analytes, or in which pockets that interact with the small analytes are enclaved by a hydrophilic network. The underlayer or enclaved pockets may interact with the small analytes through hydrophobic, acidic, basic, ionic, chelating, or $\pi-\pi$ bonding, or they may have other characteristics that cause them to interact and prevent or retard the elution of the small analytes. The present invention deals with supports having a bonded "micellar" layer, in which the micelles contain external polar and hydrophilic groups which are exposed to the mobile phase while shielding an underlayer that interacts with the small analytes. The present invention deals with a hydrophilic polymeric network that shields an underlayer that interacts with the small analytes, or such a network that contains enclaved regions that interact with the small analytes. Such hydrophilic shielding, when properly manipulated, can prevent water soluble proteins from interacting with the shielded part of the supports while allowing smaller substances to be retained or retarded by the interactive region, through hydrophobic, ionic, chelating or other interaction. These novel packings are termed shielded stationary phase (SSP).

The SSP packings of this invention are intended to eliminate the need for sample preparation procedures beyond the removal of particulate substances before the LC analysis. The packings are designed to elute the water soluble proteins, e.g. serum proteins, completely, or almost completely, in the void volume, and to retain drugs, metabolites, etc. Similarly, the packings of this invention can be used for separation of smaller analytes from water soluble proteins in the technique known as solid phase extraction, for small sample volumes to large scale industrial volumes. The SSP packing materials of the invention are conveniently produced from commercially available porous or non-porous silica supports, the surface of which is chemically modified with ligands or networks as described above. Similarly, the SSP packings can conveniently be produced from resins by modifying the surfaces of commercially available porous and nonporous materials, or by the direct preparation of such.

The use of micellar mobile phases in HPLC of proteins, e.g., nonionic surfactants, has been established in a number of studies, including use of direct plasma and serum injections (J. D. Dorsey, Chromatography 2

(1987) 13). Under these conditions, using for example a $C_{18}$ silica column, and a surfactant containing mobile phase, the surfactant saturates the stationary phase to form a double layer having a polar hydrophilic external interphase. The adsorption of many surfactants to such a reversed phase is strong enough to maintain the double layer even long after the additive has been removed from the mobile phase. Many water soluble proteins elute from such a column in the void volume, when the surfactant is selected from a groups of preferred detergents, e.g. the Tweens, bis-polyethyleneoxide derivatives of a fatty acid ester of sorbitol, as long as the double layer exists.

Albumins are known to associate with the Tweens and similar detergents below their critical micellar concentration (CMC) through hydrophobic patches located at the surface of these macromolecules, e.g. bovine serum albumin has four principal binding sites to adsorb deoxycholate, a biological "detergent" (A. Helenius, et al., Biochimica et Biophysica Acta 415 (1979) 29). A detergent-$C_{18}$ double layer can thus be drastically depleted of detergent molecules by injections of large serum samples due to the competitive adsorption of the serum albumin molecules to the surfactant.

Our invention attempts to mimic the chromatographic behavior of water soluble proteins on a "detergent modified" reversed phase by bonding appropriately designed ligands or polymeric phases to silica supports. Our invention is a new concept for chromatography in that it provides a covalently bonded micellar surface. The support consists of a non-polar spacer (R) which is interactive with small analytes and which is bonded to the support, and a hydrophilic end group (P). For a silica gel support (S) this can be represented by $(S)\equiv Si$—(R)—(P). The spacer R may be a hydrophobic moiety, in which case it will be a long chain aliphatic moiety, preferably containing 6-20 methylene groups, a crosslinked hydrocarbon, or a moiety that contains aryl groups. R may be a weak or strong anion-exchange group for ion pairing of acidic analytes, or a weak or strong cation-exchange group for ion pairing of basic analytes, or it may be a $\pi$—$\pi$ donor to associate $\pi$—$\pi$ acceptor analytes, or conversely a $\pi$—$\pi$ acceptor to associate $\pi$—$\pi$ donor analytes. It may bear chelating groups or other functional groups that will interact with the small analytes by complex formation. R may also be a combination of the groups and moieties described above. A preferred combination exists when R is a hydrophobic moiety which is substituted with weak or strong anion-exchange groups or weak or strong cation-exchange groups or $\pi$—$\pi$ donor or acceptor groups or chelating groups, or combinations of these groups. P is the hydrophilic head containing one or more polar functional groups, and $(S)\equiv Si$ is a siloxane bond (Si—O—Si) to the silica gel support. Alternatively, a hydrophilic polymeric network will shield an interactive, i.e. hydrophobic, cationic, anionic, chelating and the like, underlayer R or such a network containing interactive enclaved regions which provides a bonded phase with hydrophilic exterior, P, and interactive interior, R.

A particular advantage of the shielded stationary phase is the ability to select a phase from among the interactive underlayers or enclaved regions described above such that the retention times of particular analytes in chromatographic separations may be adjusted to resolve them from the large frontal peak of the proteins, or from other small analytes in a sample. One or more of the interactions described above may be employed to increase specific selectivity for particular analytes and make possible direct, quantitative analyses of complex mixtures such as biological matrix samples.

BRIEF DESCRIPTION OF THE DRAWINGS

FIG. 4 is a comparison of three chromatograms, A—human serum, B—propranolol (30), and C—propranolol (30) spiked human serum, as resolved upon Phase 1. N,N-bis(2'-methoxyethyl)-11-aminoundecylsilyl (see Example 1 and Table I).
Sample:
  A) 20 μl injection of human serum
  B) 1.0 μl injection containing 5 mg/ml propranolol in methanol
  C) 2.0 μl injection containing 0.2 mg/ml of 30 in human serum
Column Dimensions: 15 cm×4.6 mm
Mobile Phase: 0.5M $NH_4OAc$, adjusted to pH 6.0 with glacial acetic acid
Flow Rate: 2.0 ml/min.
Temperature: ambient
Detection: UV at 280 nm, 1.0 AUFS, ATTN 4
Chart Speed: 0.5 cm/min.

FIG. 5 is a comparison of two chromatograms, A—human serum spiked with trimethoprim (32), carbamazepine (34) and propranolol (30) and B—the same drugs in methanol, as resolved upon ω-(sulfonazide)alkylsilyl, Phase 3 (Example 3).
Sample:
  A) 10 μl injection containing a 0.2 mg/ml or each drug in a 2:2:1:solution of human serum:mobile phase:methanol
  B) 25 μl of 1 mg/ml of each drug in methanol
Column Dimensions: 5.0 cm×4.6 mm
Mobile Phase: 180 mM $NH_4OAc$:ACN (90:10) (pH 7.0)
Flow Rate: 2.0 ml/min.
Chart Speed: 0.5 cm/min.
Temperature: ambient
Detection: UV at 280 nm, 0.5 AUFS, ATTN 2

| Time | % A | % B |
| --- | --- | --- |
| 0.0 | 100 | 0 |
| 5.0 | 100 | 0 |
| 5.1 | 85 | 15 |
| 15.0 | 85 | 15 |
| 15.1 | 100 | 0 |
| 20.0 | 100 | 0 |

Flow rate: 2.0 ml/min.

Detection: UV at 285 nm, 0.032 AUFS
Chart Speed: 0.5 cm/min.

Figure 13:
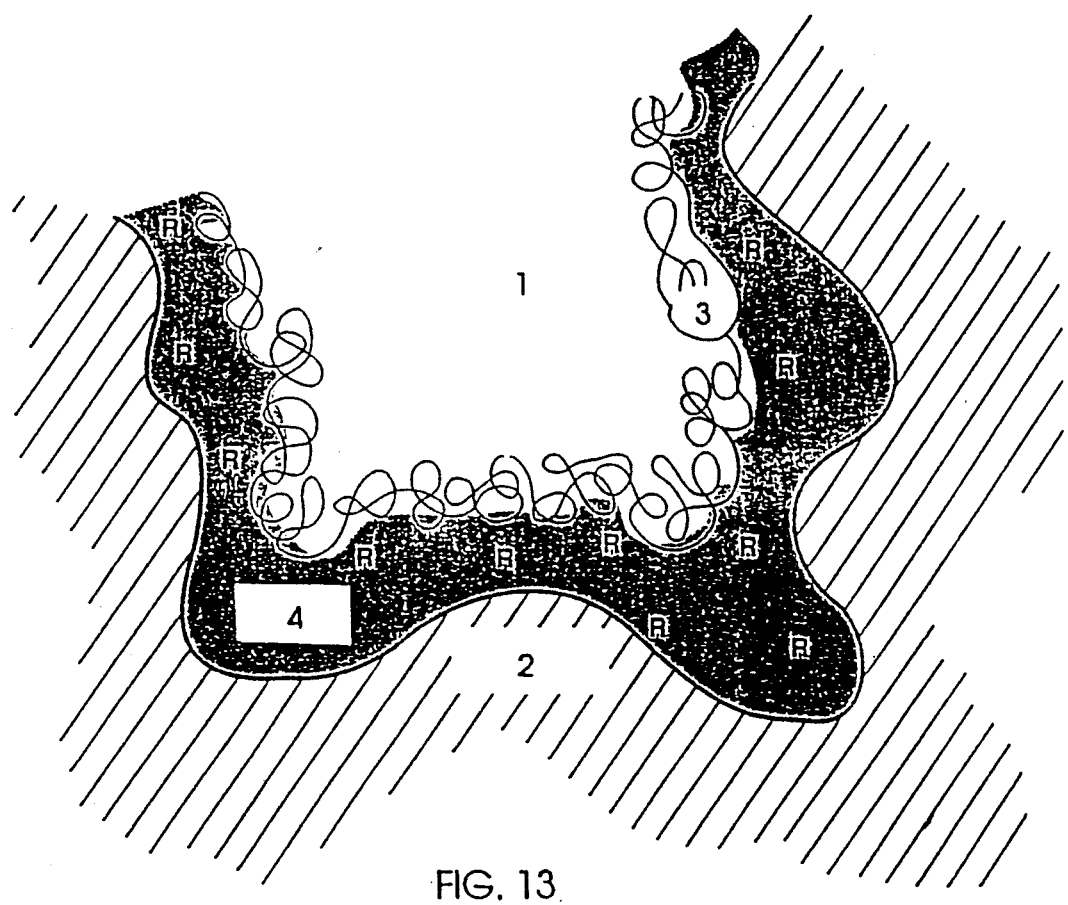

FIG. 13 represents, in schematic form, a cross-sectional view of a pore, 1, in the silica gel support, 2, with the hydrophilic shield, 3, and the shielded, interactive region, 4, which interacts with the small analytes.

DESCRIPTION OF THE PREFERRED EMBODIMENTS

Figure 1:
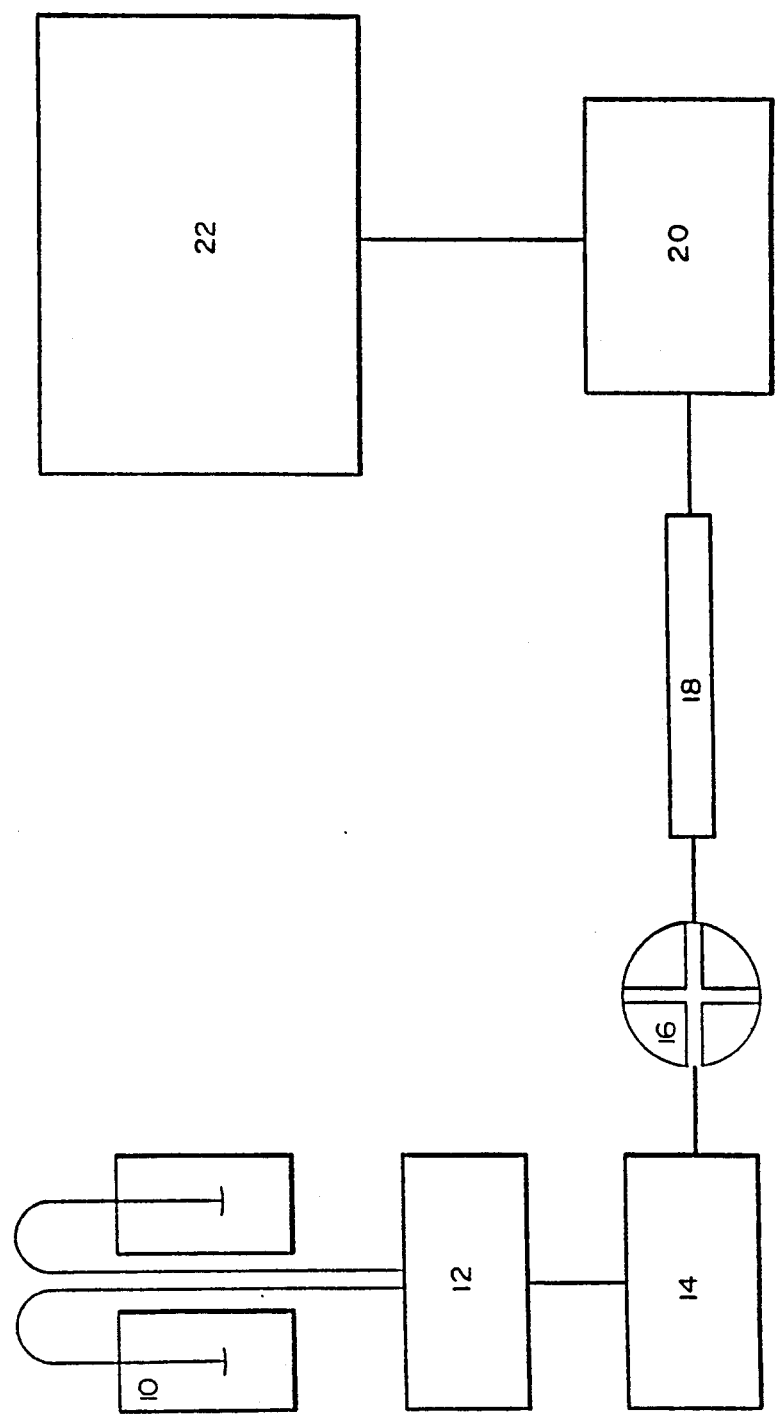
FIG. 1 schematically illustrates a typical liquid chromatography system that consists of a solvent reservoir (10), sequentially connected to a pump (12), a mixer (14), an injector (16), a column (18), a detector (20), and a recorder or data collection unit (22). The column (18) is the device that contains the shielded stationary phase involved in the chromatographic separation.

Referring to the drawings, and in particular to FIG. 1, 10 represents a solvent reservoir connected to a mixer 12 which in turn is connected to a pump 14. Pump 14 is connected to a conventional injector 16, through which the sample to be analyzed is injected into the connected column 18 which contains the shielded hydrophobic phase, the subject of this invention. The column 18 is connected to a conventional chromatographic detector 20 which in turn is connected to a recorder 22. Recorder 22 graphs the chromatogram of the sample analysis. A continuous flow of solvent proceeds from the solvent reservoir 10 through the detector 20.

Figure 2:
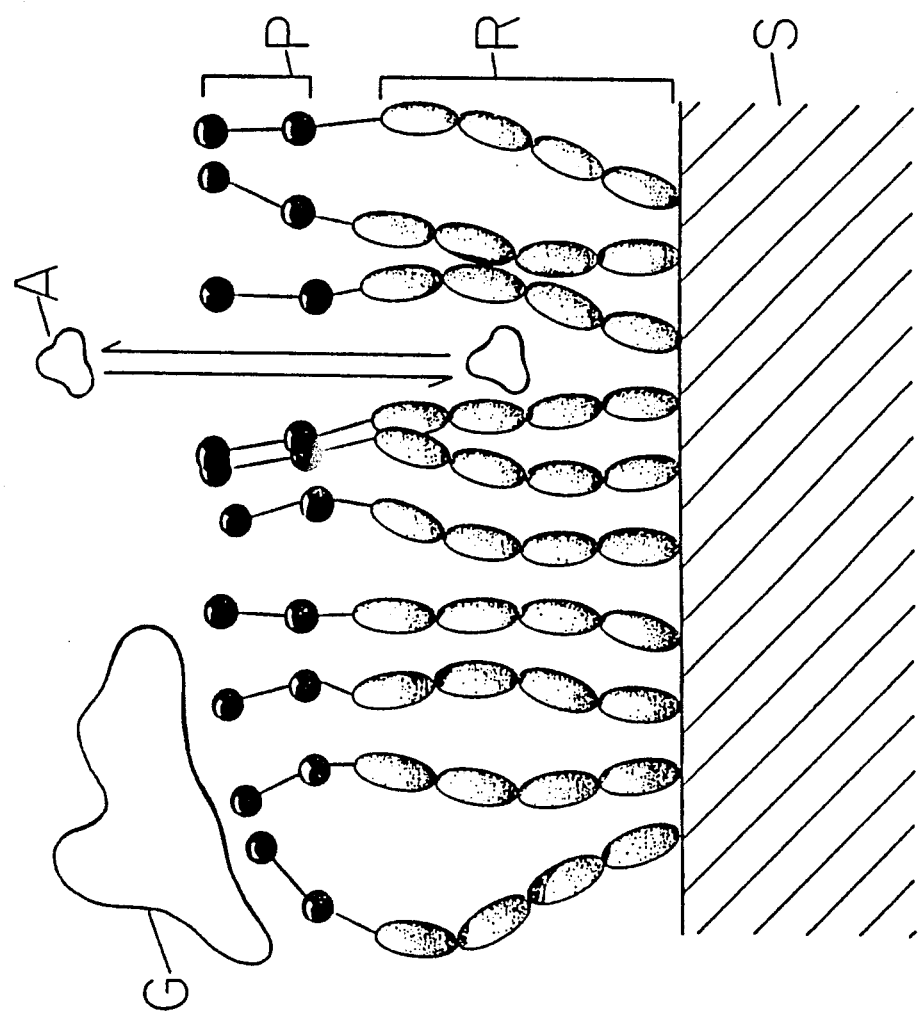
FIG. 2 schematically shows the separation mechanism of a "micellar" shielded hydrophobic phase. The external polar heads form a hydrophilic layer (P) that is exposed to the protein and shields the hydrophobic underlayer (R). The proteins (G) come in contact with the noninteracting hydrophilic layer (P) while the small analytes (A) are partitioned and retained by the hydrophobic under layer (R).

FIG. 2 schematically shows the interaction of a "micellar" shielded hydrophobic phase packed in the column 18. To the support (s) (usually silica gel) is bonded a hydrophobic spacer R.

The P groups form a hydrophilic and water solvated layer and the R groups a hydrophobic underlayer. The P layer prevents large bio-polymer molecules G from interacting with the underlayer R. Smaller analytes A may pass through and interact with the hydrophobic underlayer R.

Figure 3:
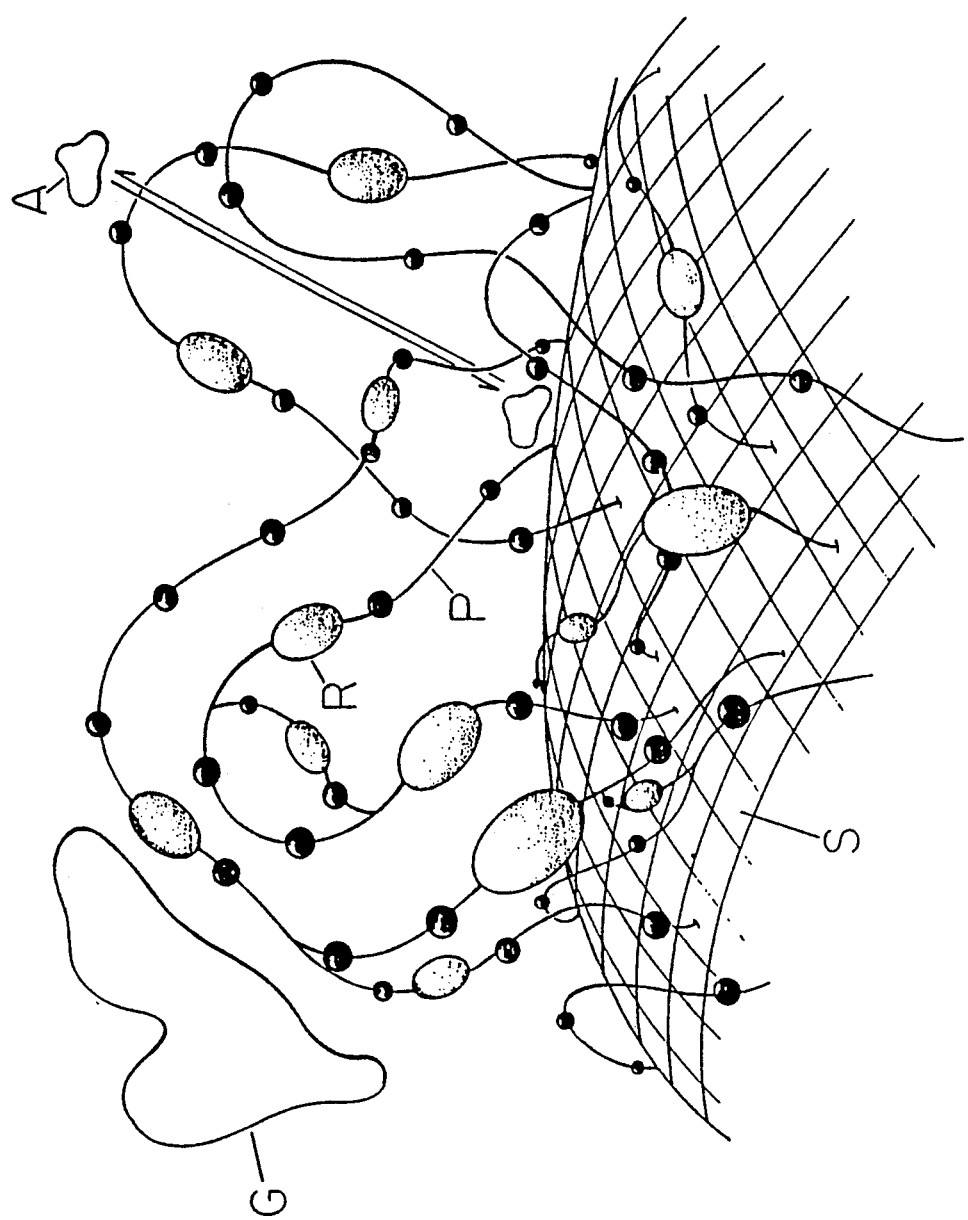
FIG. 3 schematically shows the separation mechanism of a shielded hydrophobic phase consisting of hydrophobic pockets (R) enclaved by a hydrophilic network (P). Small analytes (A) can penetrate through the network and interact with the hydrophobic pockets, while larger proteins (G) are prevented from such an interaction.
Figure 6:
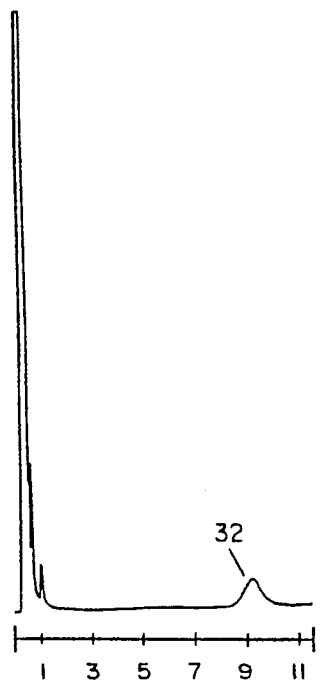
FIG. 6 shows the resolution of trimethoprim (32) from spiked calf serum as resolved upon (10-carbomethoxydecyl)dimethylsilyl. Phase 4 (Example 4).
Sample: 10 μl injection of a 1:1 calf serum: 25 mg/ml trimethoprim (32) in 10% aqueous methanol. Chromatographic conditions as described in FIG. 5, except: 0.1 AUFS, ATTN 8.
Figure 7:
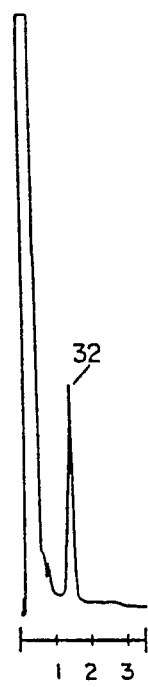
FIG. 7 shows the resolution of trimethoprim (32) from spiked calf serum as resolved upon N,N'-bis(2-hydroxyethyl)ethylenediamino modified (10-carboxydecyl)dimethylsilyl, Phase 5. Chromatographic conditions as described in FIG. 6.
Figure 8:
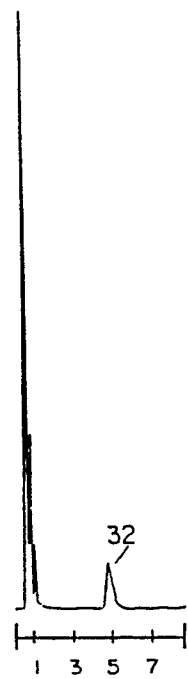
FIG. 8 shows the resolution of trimethoprim (32) from spiked calf serum as resolved upon 10 cyanodecylsilyl, Phase 6. Chromatographic conditions as described in FIG. 6.
Figure 9:
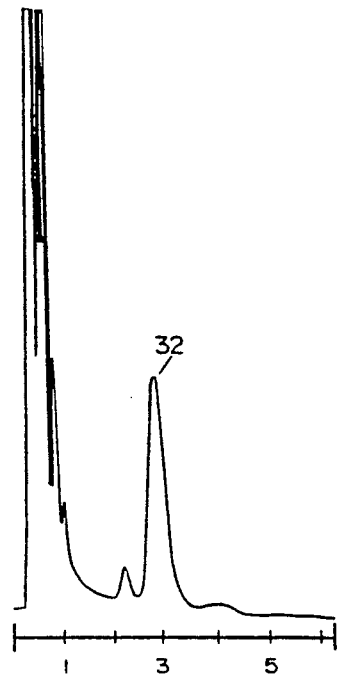
FIG. 9 shows the resolution of trimethoprim (32) from spiked calf serum as resolved upon N-(3'-propylsulfonic acid)-11-undecylaminosilyl, Phase 7 (Example 7). Chromatographic conditions as described in FIG. 6.

FIG. 3 shows a hydrophilic network P bonding the silica support (s) to hydrophobic R group (such as alkyl, aryl, etc.).

Use of a properly designed polar hydrophilic head P excludes water soluble bio-polymers, by steric hindrance, from interacting with the underlying hydrophobic spacer R. On the other hand, small analytes are "solubilized" by the R-groups as they penetrate the hydrophilic polar layer. FIG. 2 schematically shows the chromatographic interactions of SSP with a sample consisting of bio-polymer and an analyte. The polar portion of the bonded phase will screen the bio-polymer from the hydrophobic regions of the bonded phase, resulting in its rapid elution. Under the same chromatographic conditions, the smaller analyte "solubilized" by the hydrophobic regions of the bonded phase is retained and thus separated from the larger macromolecules.

FIG. 3 describes a hydrophilic water solvated network containing enclaved hydrophobic moieties R. In a similar mechanism, the larger proteins G are screened by this network from interacting with the enclaved hydrophobic moieties R which are accessible to the smaller analytes A, resulting in fast elution of the former and retention of the latter compounds.

A large variety of high performance silica gel bonded phases have been synthesized and evaluated as SSP material for direct injection of serum, plasma, or body fluids containing drugs. These phases are set forth in the following listing as Phase 1 to Phase 8 and are illustrated by Examples and/or Figures in the drawings.

FIG. 13 represents a cross-sectional view of a pore, 1, in the silica gel support, 2, with an interactive phase, 4, bonded to the support, and a hydrophilic shield, 3, which shields the interactive phase from large, water-soluble biopolymers in the liquid being analyzed. This liquid fills the pores, 1, and carries the small, hydrophobic analytes, the large, water-soluble biopolymers, and other components. The large, water-soluble biopolymers are unable to penetrate the hydrophilic shield while the small analytes are small enough to penetrate it readily and interact with the interactive phase, producing the desired chromatographic separation.

In the drawings FIGS. 4-12 represent chromatograms. The following number designations represent peaks in the chromatogram indicating the presence of the following drugs:

(30) propranolol
(32) trimethoprim
(34) carbamazepine
(36) theophylline
(38) phenobarbital
(40) ibuprofen

SILICA GEL BONDED PHASES

Phase 1≡Si(CH$_2$)$_{11}$N(CH$_2$CH$_2$OCH$_3$)$_2$
Phase 2≡Si(CH$_2$)$_{10}$CON(CH$_2$CH$_2$OCH$_3$)$_2$
Phase 3≡Si(CH$_2$)$_n$SO$_2$N$_3$ where n=7-10
Phase 4—Si(CH$_3$)$_2$(CH$_3$)$_{10}$CO$_2$CH$_3$
Phase 5—Si(CH$_3$)$_2$(CH$_2$)$_{10}$CON(CH$_2$CH$_2$OH)(CH$_2$CH$_2$NRCH$_2$CH$_2$OH) where (R)=—H and/or —CO(CH$_2$)$_{10}$Si(CH$_3$)$_2$—
Phase 6≡Si(CH$_2$)$_{10}$CN
Phase 7≡Si(CH$_2$)$_{11}$NHCH$_2$CH$_2$CH$_2$SO$_3$H
Phase 8

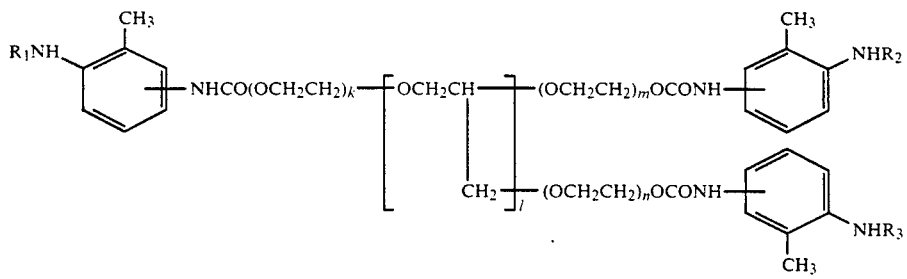

where 0≦k, l, m, n≦50, R$_1$=—CONH(CH$_2$)$_3$Si≡(S), (S)=silica gel, Si—(S)=Si—O—Si, and R$_2$, R$_3$=R$_1$ and/or another network of the same connected through a —CO— bond and/or H, and or alkyl, and/or carboxylate, and/or alkanamide.

Phase 9 A mixed phase containing Phase 8 and (S)≡Si(CH$_2$)$_3$N(CH$_3$)$_2$ in approximately equal surface concentration.

Phase 10 A mixed phase containing Phase 8 and (S)≡Si(CH$_2$)$_3$N+(CH$_3$)$_3$ in approximately equal surface concentration.

Phase 11 A mixed phase containing Phase 8 in which R$_1$ is (S)≡Si(CH$_2$)$_3$NH(CH$_2$)$_2$NHCO—, and (S)≡Si(CH$_2$)$_3$N+(C$_4$H$_9$)$_3$ in approximately equal surface concentration.

Phase 12 A mixed phase containing Phase 8 and (S)≡Si(CH$_2$)$_3$NHCO(CH$_2$)$_2$CO$_2$H in approximately equal surface concentration.

Phase 13 A mixed phase containing Phase 8 in which R$_2$ is

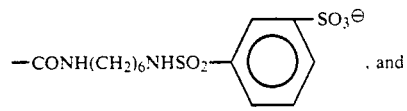, and

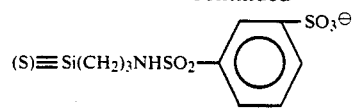

in approximately equal surface concentration.

These phases demonstrate that the interactive region of the phase, R, may be selected from a wide variety of functionalities, including but not limited to, hydrophobic, weak-base anion exchange, strong-base anion exchange, weak-acid cation exchange and strong-acid cation exchange functionalities. Phases 1 through 8 have defined hydrophobic and hydrophilic regions and are covalently bonded to the chromatographic matrix. The bonded ligand of Phases 1-7 have a hydrophobic region R consisting of a hydrocarbon chain, —(CH$_2$)$_n$— where n=6 to 20, more preferably 7 to 11 and still more preferably 10 or 11, and a polar hydrophilic head P. The hydrophobic region, R, is also referred to herein as a "leash", as it both spaces the polar group from the support and tethers the polar group to the support. Phase 8 is a bonded hydrophilic polyether network enclaving hydrophobic phenyl groups bonded to the network through bis carbamate groups.

Phases 9 through 13 have regions R and P in which R is a hydrophobic group or a weak or strong cation-exchange group or a weak or strong anion-exchange group. The preferred phase contains as regions R both regions R$_a$ which are hydrophobic, and R$_b$ which are weak or strong cation-exchange groups or weak or strong anion-exchange groups or chelating groups or π—π accepting or donating groups. R$_a$ may be any of the hydrophobic groups described herein, and preferably one of the hydrophobic groups of Phases 1 through 8. The R$_b$ group may be attached to the R$_a$ group, as for example to the nitrogen in R$_2$ or R$_3$ of Phase 8, or to the silane silicon of Phase 8, in which case the R$_b$ group is shielded by the hydrophilic polymer network of the phase. Alternatively the R$_b$ group may be attached to the silica surface through an alkylsilyl, alkylaminosilyl or alkylamidosilyl group directly, and mixed-bonded with phases 1-7, in which case it will be shielded by the hydrophilic groups of neighboring hydrophobic leash-hydrophilic head micelles. The R$_b$ group in Phase 9 is —N(CH$_3$)$_2$, a weakly basic anion exchanger; in Phase 10 it is —N+(CH$_3$)$_3$, a strongly basic anion exchanger; in Phase 11 it is —N+(C$_4$H$_9$)$_3$, another strongly basic anion exchanger; in Phase 12 it is —CO$_2$H, a weakly acidic cation exchanger; and in Phase 13 it is —SO$_3$H, a strongly acidic cation exchanger.

These phases also demonstrate that the polar head P may be selected from a wide variety of functionalities including, but not limited to: amines, amides, esters, ethers, alcohols, azides, carboxylic acids, cyano groups, thiols, diols, amino acids, nitriles, sulfonic acids, ureas, and the like, or a combination of such. All of these phases have shown retention of small drug analytes while excluding serum proteins when tested with drug containing serum. FIGS. 4-12 illustrate various chromatographic separations as carried out with different SSP supports. In a typical chromatographic separation on an SSP, the bio-polymer will elute completely, or almost completely, in the void volume, while the analyte elutes later.

The SSP supports can be simply slurry packed into standard liquid chromatography columns and used with standard HPLC equipment. Such a combination allows for the direct, on-line resolution of small analytes from a complex bio-polymer matrix in a single and simple chromatographic step. The SSP supports solve, in a new and novel way, the problem of direct, on-line analysis of analytes in bio-matrices such as serum or plasma. An example for commercial applications of this invention is the direct analysis of drugs, metabolites, etc., from serum, plasma, saliva, urine, or other body fluids as is often performed in the pharmaceutical industry, clinical and drug testing laboratories, toxicology studies, etc.

The following examples are intended to illustrate the invention, and are not to limit it except as limited by the claims. All percentages herein are by weight unless otherwise indicated, and all reagents are of good commercial quality unless otherwise indicated.

EXAMPLE 1

N,N-bis(2'-methoxyethyl)-11-aminoundecylsilyl, Phase $1 \equiv Si(CH_2)_{11}N(CH_2CH_2OCH_3)_2$ N,N-bis(2'-Methoxyethyl)-11-(triethoxysilyl)undecylamine, (II)

To a solution of 16.8 g 10-undecenal in 25 ml methylene chloride, crystals of di-$\mu$-chlorodichlorobis(ethylene)-diplatinum (II) were added and the solution heated to 40°-45° C. A solution of 16.4 g triethoxysilane in 25 ml methylene chloride was added dropwise over a period of 90 minutes. After reagent addition was completed, the rection mixture was heated for an additional 30 minutes. The mixture was fractionated and the product, 11-triethoxysilylundecanal (I) was obtained at 65° C. at 0.2 mm Hg at a 30% yield.

A solution of 6.0 g of I and 3.0 g of bis(2-methoxyethyl)amine in 100 ml absolute ethanol containing 0.25 g 10% Pd/C was hydrogenated in a Parr instrument for 90 minutes at room temperature. The mixture was filtered and the alcohol removed under reduced pressure. The residue was purified by column chromatography using 100 g dry silica gel, starting with toluene and increasing the polarity with ethyl acetate. The product, (II), eluted at 50% and 100% ethyl acetate fractions.

BONDING

A solution of (II) in 15 ml toluene was added to 4.0 g of silica gel (5-$\mu$m particle size, 100 m$^2$/g surface area, 12.5 nm average pore diameter) placed in a 50 ml glass ampule. The mixture was slurried to homogeneity and the solvent was removed under vacuum while the slurry was continuously agitated. Ammonia (gaseous) was added to the evacuated mixture, then the ampule was sealed and heated at 100° C. overnight. The mixture was thoroughly washed with methylene chloride, then methanol, and then dried. From the elemental analysis: C—6.72% (silica blank C—0.41%), a ligand coverage of 3.13 $\mu$mol/m$^2$ was calculated for $C_{17}H_{37}NO_3Si$, ($\equiv Si(OH)—(CH_2)_{11}N(CH_2CH_2OCH_3)_2$).

A 15 cm$\times$4.6 mm column was slurry packed at pressure above 52 MegaPascals. Human serum spiked with the drugs listed in Table I was directly injected through injector 16 onto column 20 containing phase 1. The column resolved the drugs from the human serum components (see Table I). FIG. 4 shows the chromatographic resolution of propranolol and other drugs from spiked human serum using the procedures of Example 1.

TABLE I

RETENTION TIMES FOR DRUGS FROM SPIKED HUMAN SERUM ON PHASE 1

| Drug | Retention Time (min.) | Mobile Phase |
|---|---|---|
| Theophylline | 1.78 | 1 |
| Propranolol | 5.00 | 1 |
| Propranolol | 2.52 | 2 |
| Quinidine | 1.97(a) | 2 |
| Carbamazepine | 33.58 | 1 |
| Carbamazepine | 12.96 | 2 |
| Desipramine | 4.25 | 2 |
| Column Dimensions: | 15 cm × 4.6 mm | |
| Flow Rate: | 2.0 ml/min. | |

1. 0.5M NH$_4$OAc aqueous solution adjusted to pH 6.0 with glacial acetic acid
2. 0.5M NH$_4$OAc pH 5.0 adjusted with H$_3$PO$_4$: 2-propanol: THF 500:25:1
(a) Not completely resolved from minor serum components

EXAMPLE 2

N,N-bis(2'-methoxyethyl)-11-silylundecanamide, Phase $2 \equiv Si(CH_2)_{10}CON(CH_2CH_2OCH_3)_2$ The material was prepared from N-hydroxysuccinimido 11-(triethoxysilyl)undecanoate which was treated with an equivalent of bis-(2-methoxyethyl)amine in methylene chloride in the presence of an equivalent of triethylamine. The product, N,N-bis-(2'-methoxyethyl)-11-(triethoxysilyl)undecanamide (III), was purified by column chromatography on a ten-fold w/w silica gel column, starting with toluene and increasing polarity with ethyl acetate. The product, an oil, eluted at 20% ethylene acetate with approximately 80% yield.

Bonding as for (II) Example 1 using 6.0 g of the same silica and impregnating with 1.65 g of (III) in 20 ml hexane yielded the N,N-bis-(2'-methoxyethyl)-11-undecanamide, Phase 2.

Elemental analysis: C—3.64, H—1.13, and N—0.40%. From the carbon percentage a coverage of 3.14 $\mu$mol/m$^2$ was calculated for $C_{17}H_{35}$—NO$_4$Si (Si(OH)—(CH$_2$)$_{10}$CON(CH$_2$CH$_2$OCH$_3$)$_2$) ligand. A 15 cm$\times$4.6 mm column was slurry packed at pressures above 52 MegaPascals. Human serum spiked with the drugs listed in Table II was directly injected through injector 16 onto column 20 containing phase 2. The column retained the drugs as listed in Table II.

TABLE II

RETENTION TIMES FOR DRUGS ON PHASE 1

| Drug | Retention Time (min.) | Mobile Phase |
|---|---|---|
| Caffeine | 1.11 | 1 |
| Acetaminophen | 1.69 | 1 |
| Propranolol | 18.01 | 1 |

(1) 0.05M ammonium acetate, 0.1M potassium chloride (pH 3.0)/MeOH 80:20

EXAMPLE 3

ω-(sulfonazido)alkylsilyl, Phase 3 $\equiv Si(CH_2)_nSO_2N_3$
n=7-10

To 10 g of SUPELCOSIL ™ silica (5-μm particle size, 10-nm pore size) in a 100 ml round bottom flask were added 10 ml of AZ-CUP MC Azidosilane reagent (Hercules, Inc., Wilmington, Del.), 25 ml of methylene chloride and 25 ml of toluene. The mixture was refluxed for eight hours, cooled, filtered, washed with 3×100 ml of methylene chloride, followed by 3×100 ml of methanol, and oven dried at 80° C. Elemental analysis: C—8.92, H—1.82, N—1.07, and S—0.58%. The resultant bonded phase was slurring packed at pressures above 34 MegaPascals into a 5 cm×4.6 mm column. Human serum spiked with the drugs listed in Table III were directly injected through injector 16, onto column 20, containing phase 3. FIG. 5 shows the chromatographic resolution of trimethoprim (32), carbamazepine (34), and propranolol (30) from the spiked human serum sample.

Table III indicates the retention time for other drugs using the procedure of Example 3.

TABLE III
RETENTION TIME FOR DRUGS AND TEST PROBES FROM SPIKED HUMAN SERUM ON THE SULFAZIDE PHASE 3

| Test Compound | Retention Time (min.) |
| --- | --- |
| Uracil | 0.37 |
| Theophylline | 0.54 |
| Caffeine | 0.71 |
| Acetaminophen | 0.54 |
| Trimethoprim (32) | 3.34 |
| Carbamazepine (34) | 4.50 |
| Codeine | 2.92 |
| Hydrochlorothiazide | 1.16 |
| Procainamide | 2.04 |
| Propranolol (30) | 13.52 |

Column Dimensions: 5 cm×4.6 mm
Mobile Phase: 180 nM NH$_4$OAc:ACN (90:10) (pH 7.0)
Flow Rate: 2.0 ml/min.

EXAMPLE 4

(10-carbomethoxydecyl)dimethylsilyl, Phase 4
—Si(CH$_3$)$_2$(CH$_2$)$_{10}$CO$_2$CH$_3$ To 5.0 g of SUPELCOSIL ™ silica (5-μm particle size, 10-nm pore size) in a round bottom flask was added 2.0 ml of (10-carboxymethoxydecyl)dimethylchlorosilane dissolved in 50 ml of dried toluene. The mixture was refluxed for 14 hours, cooled, filtered, washed with 3×100 ml of toluene followed by 3.×100 ml of methanol, and dried. Elemental analysis: C—5.66, and H—1.22%. A bonded phase coverage of 2.40 μmol/m$^2$ was calculated for C$_{14}$H$_{29}$O$_2$Si ligand. A 5 cm×4.6 column was slurry packed with this material at pressures above 41 MegaPascals. The resultant column containing phase 4 was capable of baseline resolution of trimethoprim from calf serum (FIG. 6) directly injected through injector 16.

EXAMPLE 5

N,N'-bis(2-hydroxyethyl)ethylenediamino modified 11-dimethylsilylundecanoic acid (IV), Phase 5
—Si(CH$_3$)$_2$(CH$_2$)$_{10}$CON(CH$_2$CH$_2$OH(CH$_2$CH$_2$NRC-H$_2$OH) R=H and/or CO(CH$_2$)$_{10}$Si(CH$_3$)$_2$—

A 3.8 g sample of phase 4 was hydrolyzed with 50 ml 1:1 methanol:water mix adjusted to pH 2.85 using glacial acetic acid. The mixture was shaken overnight, filtered and washed with 3×50 ml of 1:1 methanol:water, followed by 3×50 ml of methanol, and dried to yield (IV). A 3.6 g of (IV) was placed in a flask with 1.0 g of N,N'-bis(2-hydroxyethyl)ethylene diamine and 1.1 g of EEDQ (1-ethoxycarbonyl-2-ethoxy-1,2-dihydroquinoline) dissolved in 40 ml of dry THF. The mixture was shaken for six hours at room temperature. The mixture was filtered, washed with 3×100 ml of dry THF, followed by 3×100 ml of methanol, and dried. Elemental analysis:C—9.13, H—1.71, and N—1.57%. From the carbon percentage a coverage of 3.07 μmol/m$^2$ or 2.06 μmol/m$^2$ was calculated for (R=H) C$_{19}$H$_{41}$N$_2$O$_3$Si or for (R=CO(CH$_2$)$_{10}$Si(CH$_3$)$_2$—) C$_{32}$N$_{66}$N$_2$O$_4$Si$_2$, respectively. A 5.0 cm×4.6 mm column was slurry packed at pressures above 41 MegaPascals. The resulting column containing Phase 5 gave a baseline resolution of trimethoprim from calf serum (FIG. 7) when injected directly through injector 16.

EXAMPLE 6

10-cyanodecylsilyl, Phase 6 $\equiv Si(CH_2)_{10}CN$

To 10 g of oven dried SULPELCOSIL ™ silica (5-μm particle size, 10-nm pore size) in a 250 ml round bottom flask was added 2.5 ml of 10-cyanodecyltrichlorosilane and 75 ml of toluene. The mixture was refluxed for five hours and then 1.5 ml of trimethylchlorosilane was added and the mixture was refluxed an additional hour. The mixture was cooled, filtered, and washed with 3×100 ml of toluene followed by 3×100 ml of methanol, and dried.

Elemental Analysis: C—8.38, H—1.56, and N—0.98%. A bonded phase coverage of 4.03 μmol/m$^2$ was calculated for a C$_{11}$H$_{22}$NOSi ligand, ($\equiv$Si-(OH)(CH$_2$)CN).

A 5.0 cm×4.6 mm column was slurry packed at pressures above 41 MegaPascals. The resultant column containing Phase 6 gave a baseline resolution of trimethoprim from calf serum (FIG. 8) when injected directly through injector 16.

EXAMPLE 7

N-(3'-propylsulfonic acid)-11-undecylaminosilyl, Phase 7 $\equiv Si-(CH_2)_{11}NHCH_2CH_2CH_2SO_3H$ Preparation of 11-(undecylamine)trimethoxysilane According to Freifelder (J. Am. Chem. Soc. 82 (1960) 2386) by hydrogenating 10-(trimethoxysilyl)-cyanodecane in the presence of 5% Rh/alumina in 12% methanolic ammonia solution instead of ethanolic solution. The product was fractionated b.p. 145°-147° C. at 0.25 mm Hg, 50% yield.

11-Aminoundecylsilyl Phase:

5.3 g of (11-undecylamine)trimethoxysilane was dissolved in 75 ml toluene and added to 20.4 g. of SUPELCOSIL ™ silica (5-μm particle size, 10-nm pore size). The mixture was refluxed for seven hours, cooled, filtered, washed with 3.0×50 ml of toluene, followed by 3×50 ml of methanol, and dried.

Elemental analysis: C—6.68, H—1.38, N—0.54%. From the carbon percentage, a coverage of 3.38 μmol/m$^2$ was calculated for a C$_{12}$H$_{27}$NOSi ligand.

Phase 7 Preparation: to 5.0 g of the 11-aminoundecylsilyl phase dried at 65° C. under high vacuum was added 1.2 g of 1,3-propane sultone dissolved in 35 ml of methylene chloride, followed by 75 ml of methylene chloride containing 250 μl of pyridine. The mixture was shaken at room temperature for several minutes and then refluxed for three hours. The mixture was filtered, washed with 3×100 ml of methylene chloride, followed by 3×100 ml of methanol, and dried. Elemental analysis: C—8.58, H—1.60, N—1.40, and S—0.83%. From the carbon percentage, a coverage of 3.41 μmol/m² was calculated for a $C_{15}H_{33}O_3SSi$ ligand. A 5.0 cm×4.6 mm column was slurry packed at pressures above 41 MegaPascals. The resultant column containing Phase 7 gave a baseline resolution of trimethoprim from calf serum (FIG. 9) when injected directly through injector 16.

EXAMPLE 8

Urethane-modified 3-propylamine, Phase 8

where R=branched polyethylene oxide with terminal hydroxyl groups substituted with tolydiisocyanate:

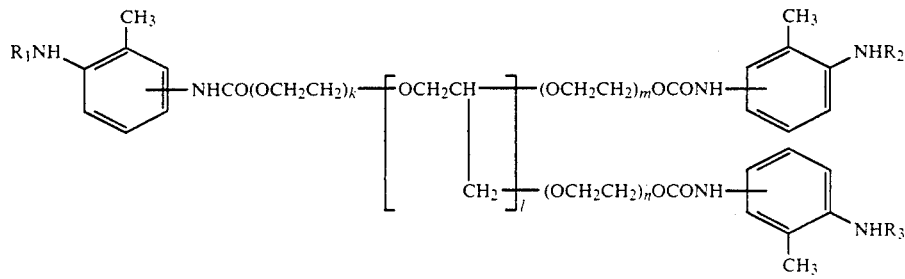

where $0 \leq k, l, m, n \leq 50$, $R_1 = \equiv SiCH_2CH_2CH_2NH-CONHR$, (S)=silica gel, Si—(S)=Si—O—Si, and $R_2$, $R_3 = R_1$ and/or another network of the same connected through a —CO— bond and/or H, and or alkyl, and/or carboxylate, and/or alkanamide.

To 30 g of dry SUPELCOSIL silica (5-μm particle size, 10-nm pore size) 20 g of 3-aminopropyltrimethoxysilane and 300 ml of toluene were added. The suspension was heated to reflux for 16 hours, and the reaction mixture was filtered and washed with 300 ml of toluene followed by 300 ml of methanol and dried at 60° C. under nitrogen for 10 hours.

To 600 ml of toluene in a 1000 ml round bottom flask was added 5.0 g of Hypol FHP 2000 polymer (W. R. Grace, Co., Lexington, Mass.). The polymer was completely dissolved by shaking and sonicating. To the solution 12.5 g of the 3-aminopropyltrimethoxysilane-bonded silica from the step above was added. The suspension was refluxed for three hours. To the mixture was added 0.2 g of 1,4-diazabicyclo-(2,2,2)octane dissolved in 10 ml of toluene, and the mixture was refluxed for an additional three hours. The "hot" mixture was filtered, washed with toluene, methylene chloride and methanol, and oven dried. Elemental analysis: C—10.41, H—1.66, and N—1.30%.

Figure 10A:
FIG. 10 shows three chromatograms, A—theophylline (36), B—phenobarbital (38), and C—carbamazepine (34) of spiked calf serum at or below the therapeutic levels as resolved upon Phase 8 (Example 8).
Sample: 10 μl injection containing 10 μg/ml of each drug in calf serum
Column Dimensions: 15 cm × 4.6 mm
Mobile Phase:
  A—180 mM NH₄OAc,
  B and C—180 mM NH₄OAc/ACN 95:5
Flow Rate: 2.0 cm/min.
Detection: UV at 254 nm, 0.001 AUFS, ATTN 8
Chart Speed: 5 mm/min.
Figure 10B:
Figure 10C:
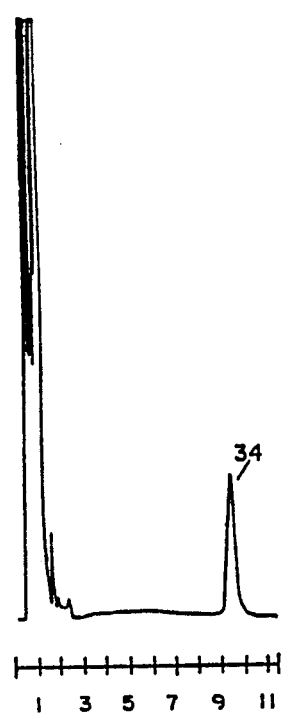
Figure 11A:
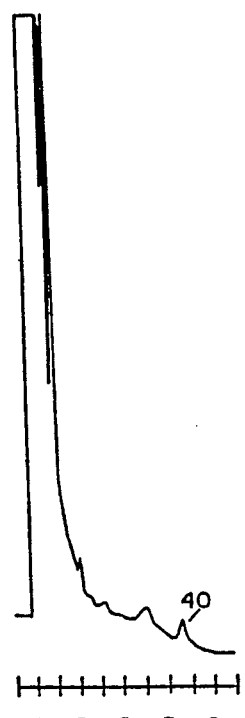
FIG. 11 is a comparison of two chromatograms. A—ibuprofen (40) in human serum after Advil ® ingestion and B—ibuprofen (40) standard, upon Phase 8 (Example 8).
Sample:
  A—10 μl of human serum taken from a blood sample 90 minutes after ingestion of two Advil tablets
  B—5 μl of ibuprofen standard (0.5 mg/ml in methanol)
Column Dimensions: 15 cm × 4.6 mm
Mobile Phase: 180 mN NH₄OAc/ACN/THF 95:5:1
Flow Rate: 2.0 ml/min.
Chart Speed: 5 mm/min.
Detection: UV at 273 nm, 0.001 AUFS, ATTN 4
Figure 11B:
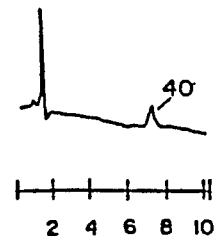
Figure 12A:
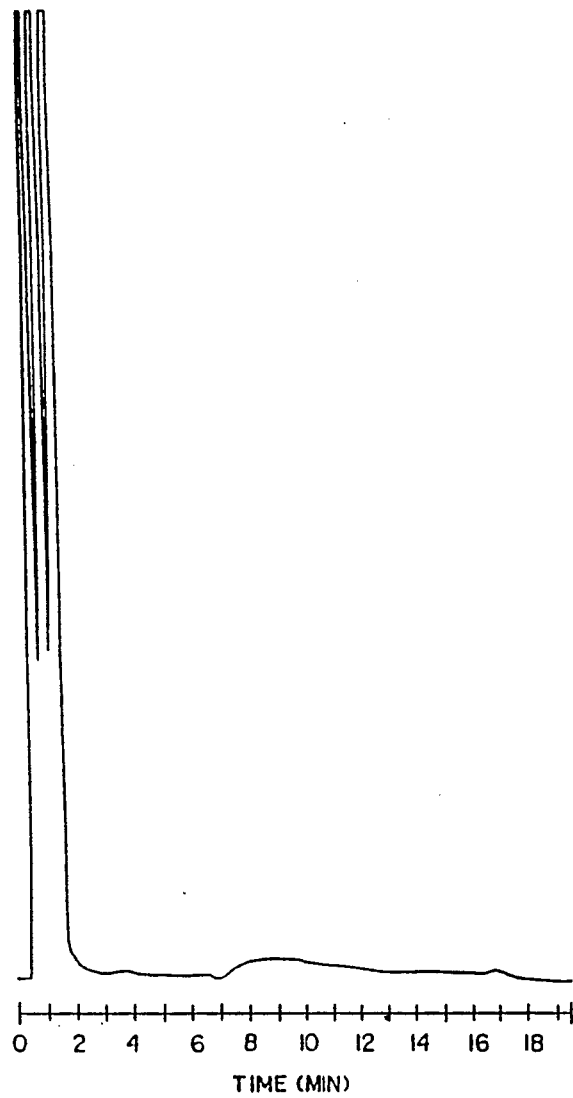
FIG. 12 shows the purification of carbamazepine (34) form spiked calf serum upon Phase 8 (Example 8).
Sample:
  250 μl injection of 5 μg/ml carbamazepine (34) in calf serum.
  A—1.0 ml fraction was collected and 250 μl reinjected the protein containing fraction.
  B—The carbamazepine (34) fraction was collected in a 2 ml fraction and 250 μl of the carbamazepine (34) fraction was reinjected (0.625 μg/ml)
Column Dimensions: 15 cm × 4.6 mm
Mobile Phase:
  A—180 mM NH₄OAc
  B—ACN
Gradient Profile.
Figure 12B:
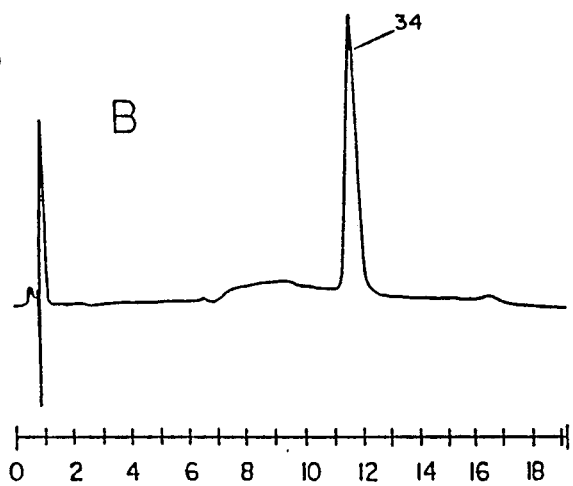

A 15 cm×4.6 mm column was slurry packed at pressures above 52 MegaPascals. The column resolved various drugs from calf and human sera. FIG. 10 shows carbamazepine-, phenobarbital- and theophylline-spiked human serum samples as resolved on a column containing Phase 8 by directly injecting the spiked samples through injector 16. FIG. 11 shows the resolution of ingested ibuprofen from human serum. FIG. 12 shows the trace enrichment/purification by a step-wise elution of a carbamazepine-spiked calf serum and the chromatographic results of the collected protein and drug containing fractions. This evaluation demonstrates the application of the packing material for trace enrichment, which could be applied in solid phase extraction of small volumes up to large scale industrial levels.

EXAMPLE 9

$R = -N(CH_3)_2$, Phase 9

To 7.12 g of SUPELCOSIL TM DB silica (5μm particle size, 10 nm pore size) previously conditioned at 85% humidity (allowing to equilibrate over a saturated aqueous solution of lithium chloride) were added 5.6 mmole (1.16 g) of N,N-dimethyl-3-aminopropyltrimethoxysilane, 5.6 mmole (1.0 g) 3-aminopropyltrimethoxysilane and 100 ml toluene. The mixture was suspended and refluxed for 4 hours. The mixture was filtered, and the solid material was washed with 200 ml toluene, then 200 ml methylene chloride, and finally 200 ml methanol. The solid product was dried at 60° C. under nitrogen for four hours followed by two hours at high vacuum. To the dried solid product a solution of 2.8 g Hypol FHP 2000 polymer (W. R. Grace Company, Lexington, Mass. in 100 ml of dry toluene was added. The mixture was suspended and refluxed for one hour; 1.0 ml of hexylamine was added and suspended, and the mixture was refluxed for one additional hour. The solid product was filtered hot and washed with 200 ml each of toluene, methylene chloride and methanol. The solid product was dried at 60° C. under nitrogen for four hours. To the solid product 50 ml of dry pyridine and 4.0 ml of acetic anhydride were added. The mixture was agitated for 10 hours, then filtered and washed with 100 ml toluene, 200 ml methylene chloride and 300 ml methanol. The solid product was dried at 60° C. under nitrogen for four hours.

Elemental analysis: C—14.95%; H—2.33%; N—1.99%.

A 4.6-mm×15-cm column was slurry packed at 59 MegaPascals with Phase 9. The operating conditions and results of chromatographic separations of serums spiked with chloramphenicol, salicylic acid and benzoic acid are shown in Table IV, below.

EXAMPLE 10

$R = -N^+(CH_3)_3$, Phase 10

Phase 10 was prepared according to the procedure of Example 9, above, except that 3 μmole per square meter of silica surface of a 50% methanolic solution of N-(3-trimethoxysilylpropyl)trimethylammonium chloride was used in place of the N,N-dimethyl-3-aminopropyltrimethoxysilane, and 3 μmol per square meter of silica surface of the 3-aminopropyltrimethoxysilane was used.

Elemental analysis: C—15.83% and N—1.92%.

A 4.6-mm×15-column was slurry packed at 59 MegaPascals with Phase 10. The operating conditions and results of chromatographic separations of serums spiked with chloramphenicol, salicylic acid and benzoic acid are shown in Table IV, below.

EXAMPLE 11

R=—N+(C4H9)3, Phase 11

Phase 11 was prepared according to the procedure of Example 9, except that 3 μmole per square meter of silica surface of a 50% methanolic solution of N-(3-trimethoxysilylpropyl)tributylammonium bromide and 3 μmole per square meter of silica surface of N-(2-aminoethyl)-3-aminopropyltrimethylsilane were substituted for the N,N-dimethyl-3-aminopropyltrimethoxysilane and 3-aminopropyltrimethoxysilane of Example 9.

Elemental analysis: C—15.85% and N—2.40%

A 4.6-mm×15-cm column was slurry packed at 59 MegaPascals with Phase 11. The operating conditions and results of chromatographic separations of serums spiked with chloramphenicol, salicyclic acid and benzoic acid are shown in Table IV, below.

TABLE IV
CAPACITY FACTOR RESULTS FOR CHROMATOGRAPHIC SEPARATION WITH BASIC MODIFIED PHASE 8

| Separated Component | Phase 8 | Phase 9 | Phase 10 | Phase 11 |
|---|---|---|---|---|
| Chloramphenicol | 2.54 | 4.04 | 5.61 | 5.20 |
| Salicylic Acid | 2.05 | 5.20 | 10.20 | 23.19 |
| Benzoic Acid | 1.16 | 2.19 | 3.66 | 4.44 |
| Total Serum Protein Area. (million counts) | 11.5 | 10.8 | 11.6 | 12.0 |

Chromatographic Conditions

Mobile Phase: 95% 180 mM NH4OAc (aq) pH=7.0/5% AcN
Flow: 2.0 ml/min
Injection Volume: 10 μl
Concentration and Detection:
 Chloramphenicol, 10 μg/ml, 278 nm, 0.016 AUFS
 Salicylic Acid, 25 μg/ml, 280 nm, 0.008 AUFS
 Benzoic Acid, 10 μg/ml, 254 nm, 0.016 AUFS or 0.032 AUFS
 Serum, neat, 254 nm, 0.016 AUFS
Temperature: Ambient.
NOTE—The Capacity factor, $C_i$, is defined as $$C_i = \frac{V_i - V_o}{V_o}$$

where $V_i$ is the elution volume of compound i and $V_o$ is the elution volume of an unretained compound ($V_o$ is also termed the void volume).

EXAMPLE 12

R=—CO2H, Phase 12

Phase 12 was prepared according to the procedure of Example 9, except that only 20 μmole per square meter of silica surface of the 3-aminopropyltrimethoxysilane and no other aminosilane was used; subsequent to the addition of the pyridine but prior to the addition of the acetic anhydride, 0.15 g/g of silica of succinic anhydride was added and the mixture was agitated for 22 hours; and in the final washing of the solid product the first rinse was with water, followed by 50% aqueous methanol and finally methanol.

Elemental analysis: C—16.69%, H—2.48%, and N—2.23%.

A 4.6-mm×15-cm column was slurry packed at 59 MegaPascals with Phase 12. The operating conditions and results of chromatographic separations of serums spiked with chloramphenicol, salicylic acid and benzoic acid are shown in Table V, below.

EXAMPLE 13

R=—SO3H, Phase 13

Phase 13 was prepared according to the procedure of Example 12, except that the reaction mixture was cooled to room temperature and instead of the hexylamine, a solution of 1.5 g hexamethylenediamine in 50 ml of toluene for each 10 g of silica gel was added and the mixture was agitated for three hours. In addition, prior to adding the acetic anhydride the solid product is dried under high vacuum at 60° C. for two hours; 4 μmole per square meter of silica surface of 3-fluorosulfonylbenzenesulfonyl chloride was substituted for the succinic anhydride; and following the final washing step the solid product was dried under high vacuum at 60° C. for two hours. A calculated amount of 3 μmole per gram of silica, based on the pretreatment weight of silica used in this example, of tetrabutylammonium hydroxide in a 40% aqueous solution was evaporated to dryness under vacuum for three hours at ambient temperature, dissolved in 4 ml/g of silica of dry pyridine, and added to the silica. The mixture was agitated at room temperature for 20 hours, filtered and washed thoroughly with 1:9 acetonitrile:water containing 180 mmole ammonium acetate, followed by washing with water and then methanol. The solid product was dried at 60° C. under nitrogen for four hours.

Elemental analysis:
 Prior to final treatment step- C—16.14%, H—2.48%, N—2.35%, S—0.75% and F—0.20%
 Final product- C—16.19%, H—2.48%, N—1.83%, S—0.55% and F—0.050%.

Despite the presence of fluoride in the final product, the material that was almost completely inactive to ion exchange prior to the tetrabutylammonium hydroxide treatment became an active ion-exchange material following this treatment.

A 4.6-mm×15-cm column was slurry packed at 59 MegaPascals with Phase 13. The operating conditions and results of chromatographically separating a mixture of chloramphenicol, salicylic acid and benzoic acid are shown in Table V, below.

TABLE V
CAPACITY FACTOR RESULTS FOR CHROMATOGRAPHIC SEPARATION WITH ACID-MODIFIED PHASE 8

| Separated Component | Phase 8 | | Phase 12 | | Phase 13 | |
|---|---|---|---|---|---|---|
| | pH 7 | pH 4 | pH 7 | pH 4 | pH 7 | pH 4 |
| Chloramiphenicol | 2.54 | 2.25 | 3.79 | 3.16 | 4.06 | 3.53 |
| Trimethoprim | 2.56 | 0.30 | 4.83 | 0.25 | 4.02 | 2.21 |
| Propranolol | 2.94 | 0.85 | 8.40 | 0.76 | 9.80 | 6.00 |
| Total Serum Protein Area (million counts) | 11.5 | 11.1 | 11.7 | 12.0 | 11.4 | 10.0 |

Chromatographic Conditions

Mobile Phase:

for pH 7—95% 180 mM NH4OAc (aq) pH=7.0/5% AcN for pH 4—95% 90 mM NH4OAc (aq) pH=4.0/5% AcN Flow: 2.0 ml/min Injection Volume: 10 μl Concentration and Detection:
 Chloramphenicol, 10 μg/ml, 278 nm, 0.016 AUFS
 Trimethoprim, 25 μg/ml, 254 nm, 0.016 AUFS
 Propranolol, 25 μg/ml, 254 nm, 0.016 AUFS
 Serum, neat, 254 nm, 0.016 AUFS Temperature: Ambient.

NOTE—Chloramphenicol, trimethoprim and propranolol values were determined in a serum matrix.

We claim:

1. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

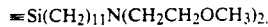
$\equiv Si(CH_2)_{11}N(CH_2CH_2OCH_3)_2$.

2. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

$\equiv Si(CH_2)_{10}CON(CH_2CH_2OCH_3)_2$.

3. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

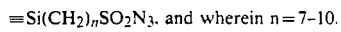
$\equiv Si(CH_2)_nSO_2N_3$, and wherein n=7–10.

4. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

$-Si(CH_3)_2(CH_2)_{10}CO_2CH_3$.

5. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

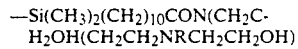
$-Si(CH_3)_2(CH_2)_{10}CON(CH_2CH_2OH)(CH_2CH_2NRCH_2CH_2OH)$ and wherein $R = -CO(CH_2)_{10}Si(CH_3)_2-$.

6. A shielded stationary-phase packing material useful for liquid chromatography analysis and/or solid-phase extraction of a mixture containing proteinaceous compounds and small analytes, comprising:
 a porous, silica-gel support;
 and bonded to the support a phase having
  (a) a hydrophobic internal leash bonded to the support and bearing functionality that interacts with the small analytes; and
  (b) an external hydrophilic moiety bonded to the internal leash to form a hydrophilic external layer;
whereby the external hydrophilic external layer forms a water solvated interface which allows the small analytes to diffuse and interact with the internal leash but prevents interaction between the internal leash and the proteinaceous compounds, the phase being represented by the formula:

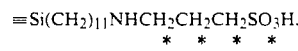
$\equiv Si(CH_2)_{11}NHCH_2CH_2CH_2SO_3H$.

* * * * *